United States Patent [19]

Perry et al.

[11] Patent Number: 4,471,220

[45] Date of Patent: Sep. 11, 1984

[54] SYSTEM FOR MONITORING TRACE GASEOUS AMMONIA CONCENTRATION IN FLUE GASES

[75] Inventors: Bruce N. Perry, Maplewood; Alexander Stein, Secaucus, both of N.J.

[73] Assignee: Exxon Research and Engineering Co., Florham Park, N.J.

[21] Appl. No.: 332,476

[22] Filed: Dec. 21, 1981

[51] Int. Cl.³ .................. G01J 1/00; G01N 21/35
[52] U.S. Cl. ................................ 250/339; 356/51
[58] Field of Search ............. 356/51, 407, 437–439; 250/339, 343–345

[56] References Cited

U.S. PATENT DOCUMENTS 3,766,380 10/1973 Menzies .............................. 250/343
3,958,122 5/1976 Jowett et al. ................... 250/344 X

OTHER PUBLICATIONS

Shumate, Conference: International Telemetering Conference, Los Angeles, CA, U.S.A. (Oct. 15–17, 1974), pp. 388–396.

Primary Examiner—F. L. Evans
Attorney, Agent, or Firm—Ronald D. Hantman

[57] ABSTRACT

A system is disclosed for monitoring the concentration of gaseous ammonia in flue gases by simultaneously measuring the temperature and optical transmission of a flue gas-ammonia mixture.

3 Claims, 4 Drawing Figures

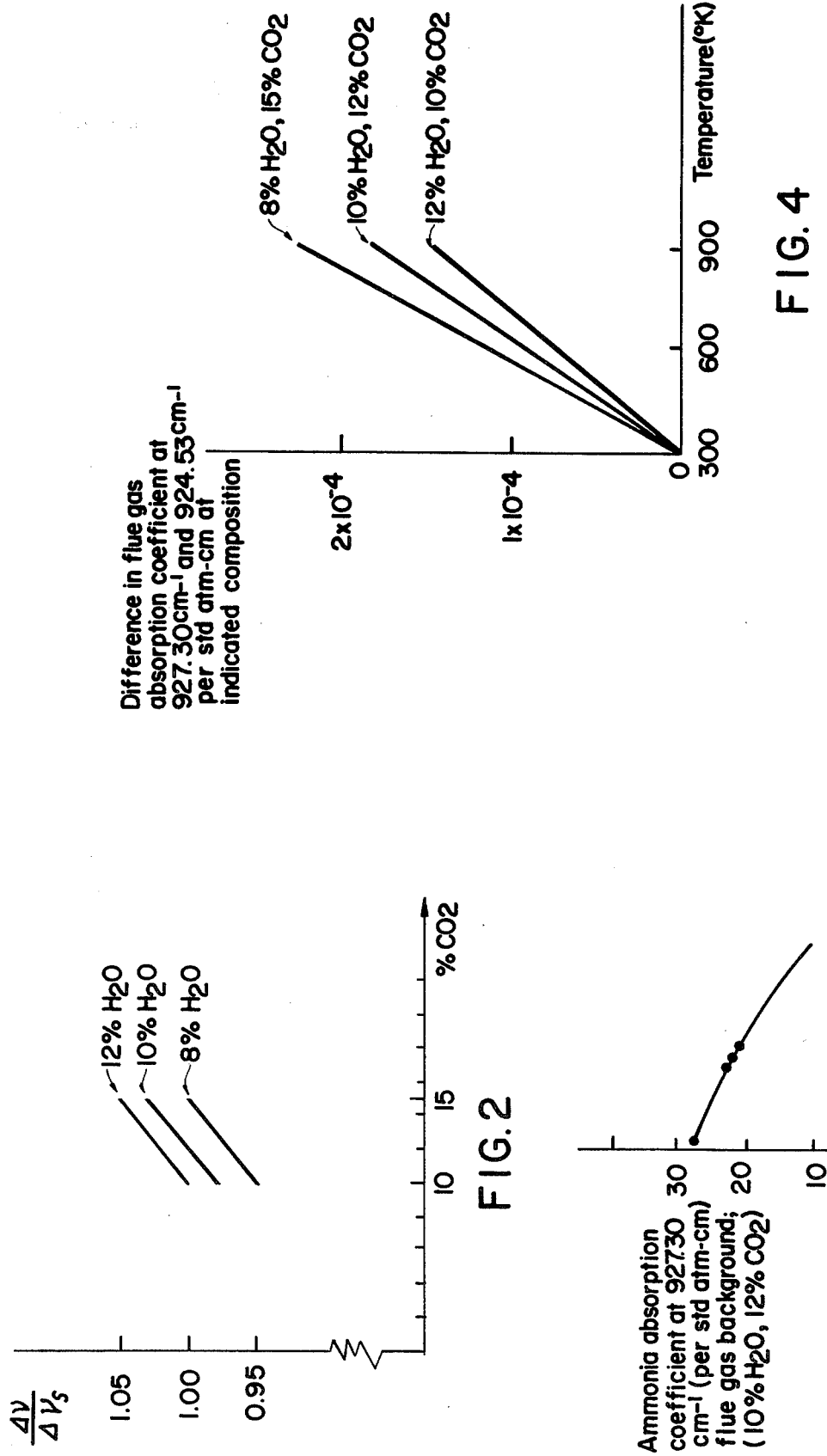

SYSTEM FOR MONITORING TRACE GASEOUS AMMONIA CONCENTRATION IN FLUE GASES

FIELD OF THE INVENTION

This invention relates to means for remotely determining absolute ammonia concentration using lasers.

BACKGROUND OF THE INVENTION

It is desirable to be able to measure the gaseous ammonia concentration in a variety of environments. In particular, it is often desirable to continuously monitor gaseous ammonia in situ in such environments as flue gas, chemical plant feedstreams and atmospheric backgrounds. In fact, it has been mandated to continuously monitor the ammonia concentration in flue gases resulting from deNox processes which introduce ammonia to the combustion products in order to accomplish conversion of oxides of nitrogen to $N_2$ and $H_2O$. In such processes the level of ammonia which must be detected is as low as 5 parts per million.

Using standard techniques which require point sampling of the gases poses the difficult problem of avoiding plugging of sampling systems, which may happen by physical blockages, due to e.g., fly ash in coal-fired boilers, or by deposition of chemical reaction products (e.g. ammonium-sulfates or sulfites) in the sampling system. This latter problem may be alleviated by raising the temperature of the sampling system, but the possibility of residual reactions causing changes in ammonia concentration during transport of the gaseous sample from a flue duct to a measuring system introduces an uncertainty into how accurately the same as analyzed represents the flue gas. In addition, techniques which sample a single point assume a homogeneous ammonia distribution within the sampled ducts.

In the present invention, infrared laser absorption is employed as a remote diagnostic of ammonia concentration, in part to obviate problems associated with sampling systems.

It is known that optical absorption due to ammonia depends upon optical wavelength, ammonia concentration, and optical path length, and that absorption of optical radiation from lasers can be used to detect the presence of ammonia in an atmospheric background.

In an article entitled "Measurements of NH$_3$ Absorption Coefficients With a $C^{13}O_2^{16}$ Laser", by Messrs. Allario and Seals, appearing in *Applied Optics*, Volume 14, No. 9, September 1975 at page 2229 (which article is incorporated herein by reference as though fully set forth herein) it was found that absorption of certain $C^{13}O_2^{16}$ laser wavelengths could be directly related to ammonia concentration. It was also found that certain other laser transitions were only negligibly absorbed by ammonia in an atmospheric background, and it was noted that transmission of these wavelengths could be used to distinguish ammonia absorption from scattering or absorption by atmospheric particulates or variations in refractive index, since such interfering mechanisms would attenuate all $CO_2$ laser wavelengths nearly equally.

The prior art does not provide a prescription for the construction of a device useful for monitoring trace NH$_3$ concentrations in a hot flue gas background, for several reasons. First, the coefficient relating optical absorption by NH$_3$ molecules to their concentration depends on both the line strength and the spectral width of the probed NH$_3$ line. The line strength depends on a population difference and thus on temperature. The line width varies with both temperature and composition (percentages of $H_2O$ and $CO_2$) of the flue gas, which in turn change with the type of combustion, amount of excess air, and location of sampling point. Furthermore, the lowest level of NH$_3$ which can be detected is limited by the existence of a small difference in absorption from the $H_2O$ and $CO_2$ present in the flue gas itself at the two wavelengths selected for monitoring. This residual absorption represents a zero level for the NH$_3$ measurement. As the flue gas composition and temperature vary, so does this zero level, thereby limiting the sensitivity of the NH$_3$ detection.

One would therefore assume that both the composition and the temperature of the flue gas must be monitored together with optical absorption to determine NH$_3$ concentration with an adequate degree of sensitivity and accuracy. A system capable of monitoring $CO_2$ and $H_2O$ concentration, temperature, and optical absorption would be so complex and costly as to render the method impractical. The present invention demonstrates, however, that measurements of flue gas temperature and optical absorption suffice to determine NH$_3$ concentrations in flue gas to the 5 ppm level even if the flue gas $H_2O$ and $CO_2$ composition is uncertain within typical limits.

BRIEF DESCRIPTION OF THE INVENTION

In accordance with the present invention, a system for determining the absolute concentration of gaseous ammonia occurring in an environment of flue gases, which may vary in temperature, is disclosed. The system provides measurement of the transmission of radiation at a first wavelength which is strongly absorbed by ammonia but is negligibly absorbed by all other substances in a mixture of flue gases, measurement of transmission of radiation at a second wavelength which is negligibly absorbed by ammonia and by all other substances in a mixture of flue gases, and measurement of the temperature of the optically absorbing flue gases.

The system of this invention directs radiation at both a first and a second wavelength along an optical path through a flue gas duct and to a detector of radiation, and measures optical transmission at each of these wavelengths. The system measures flue gas temperature by other means. The system then computes ammonia concentration from the measurements of optical transmission and temperature, together with stored data for the ammonia absorption coefficient at the measured temperature. The data are disclosed herein for a preferred embodiment of the invention.

DESCRIPTION OF THE DRAWINGS

For a more complete understanding of the invention reference should be made to the following detailed description and drawings wherein:

FIG. 2 is a graph showing the linewidth of the $Q_a(6,6)\nu_2$ ammonia transition at 927.30 cm$^{-1}$, normalized to its value at 10% $H_2O$ and 12% $CO_2$ background composition, at a fixed temperature.

FIG. 3 is a graph showing a portion of the data stored in the computing means 20 of FIG. 1 which is required for the proper operation of a preferred embodiment of the invention, and is a graph of ammonia absorption at 927.30 cm$^{-1}$ as a function of temperature for a flue gas background.

FIG. 4 is a graph showing additional data required for the proper operation of a preferred embodiment of the invention, and is a graph of the difference in flue gas absorption coefficient at two wavelengths.

DETAILED DESCRIPTION OF THE INVENTION

Figure 1:
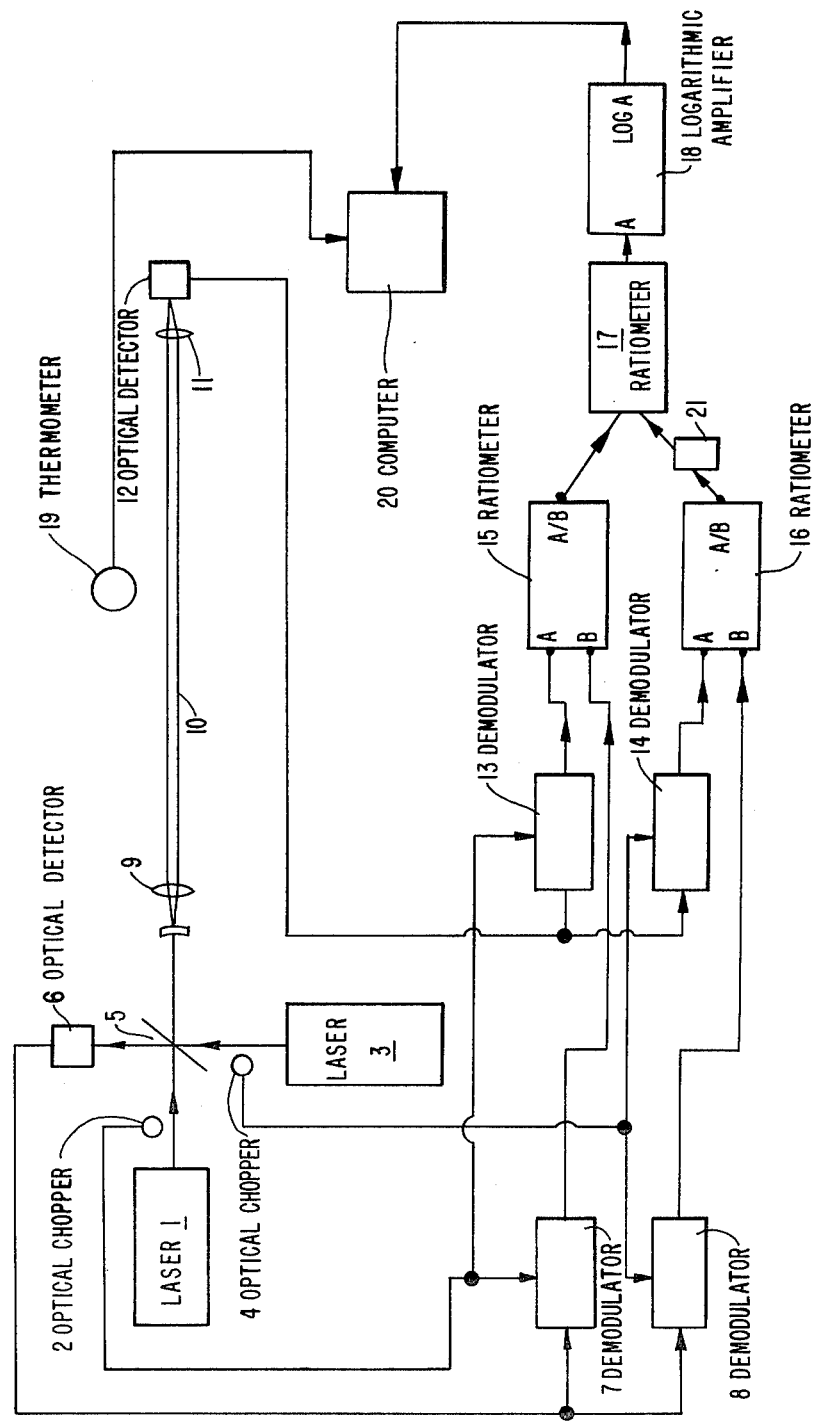
FIG. 1 is a view in schematic form, showing a device constructed in accordance with the teachings of this invention.

Referring now to FIG. 1, we see a preferred embodiment of the invention which provides a continuous measurement of ammonia concentration. $CO_2$ laser 1 emits radiation of 927.30 cm$^{-1}$, which is periodically interrupted by optical chopper 2 at frequency $f_1$. The 927.30 cm$^{-1}$ radiation is coincident with the $Q_\alpha(6,6)\nu_2$ transition of ammonia. $CO_2$ reference laser 3 emits radiation of 924.53 cm$^{-1}$, which is periodically interrupted by optical chopper 4 at a frequency $f_2$. The reference 924.53 cm$^{-1}$ radiation is essentially not absorbed by ammonia or any other substances present in flue gas. The reference laser corrects for absorption which is not spectrally selective, due to, e.g., turbulence, soot, or particulates. The reference and sample choppers operate at different frequencies so that the signals may be separated electronically. The $CO_2$ laser beams are directed to a common point on beam container 5, which is a partially transmitting, partially reflecting optical element or other beam combining means. A portion of each of the laser beams falls on optical detector 6, thus producing an electrical signal proportional to optical intensity received. This signal is sent to demodulators 7 and 8, which detect signals modulated at frequencies $f_1$ and $f_2$, which are signals respectively proportional to the output powers of lasers 1 and 3. The proportionality constant may be chosen to have an convenient value. In FIG. 1, demodulators 7, 8, 13 and 14, are provided with phase reference input signals indicated by arrows on their left sides, modulated input signals indicated by arrows on their top sides, and produce output signals indicated by arrows on their right sides.

The remaining portion of each of the laser beams from lasers 1 and 3 now pass through beam expander and collimator 9, and thence through a flue gas region 10 to be monitored for ammonia concentration. The beams are then focused by lens 11 onto detector 12. The resulting electrical signal from optical detector 12 is sent to demodulators 13 and 14, which detect signals proportional to the transmitted optical powers from lasers 1 and 3 respectively. Ratiometer 15 takes as inputs voltage signals which are proportional to incident and transmitted radiation of 927.30 cm$^{-1}$ and outputs a voltage signal proportional to optical transmission for radiation of 927.30 cm$^{-1}$. Ratiometer 16 similarly produces a signal proportional to optical transmission for radiation of 924.53 cm$^{-1}$. In FIG. 1, the letters A and B represent input signals and A/B indicates the function produced by ratiometers 15, 16, and 17. Electrical attenuator 21 adjusts the two inputs to ratiometer 17 to be equal when no ammonia is present in region 10, to correct for an unequal division of optical power by beam combiner 5. In FIG. 1, the attenuator 21 is shown so as to attenuate signal B into 17. However, the attenuator 21 may be placed to attenuate either input A or B of ratiometer 17 according to which wavelength is preferentially transmitted by beam combiner 5. Ratiometer 17 produces a signal proportional to the ratio of optical transmittances for radiation of 924.53 cm$^{-1}$ and 927.30 cm$^{-1}$. Logarithmic amplifier 18 produces a voltage proportional to ammonia concentration, through a proportionality factor which depends on the temperature of the flue gas in region 10. Thermometer 19 (e.g. a thermocouple) produces a voltage uniquely related to the temperature of the sampled region 10. Finally computer 20 determines the ammonia concentration in region 10 using input absorption and temperature data, together with a stored algorithm which relates absorption coefficients to temperature through the data of FIGS. 3 and 4, which are described below.

Thus, the system relates optical absorption to $NH_3$ concentration for a measured temperature even if the concentration of $H_2O$ and $CO_2$ in the flue gas is uncertain within a typical range defined below.

This is illustrated by the data of FIGS. 2, 3 and 4. FIG. 2 is a plot of the relative linewidth of the $Q_\alpha(6,6)\nu_2$ transition of $NH_3$ occurring at 927.30 cm$^{-1}$, for various $H_2O$ and $CO_2$ background gas compositions, normalized to the value of linewidth for 10% $H_2O$ and 12% $CO_2$. The data were obtained by measuring the ammonia linewidth using a tunable diode laser in mixtures containing differing amounts of $CO_2$ and $H_2O$ vapor. The data of FIG. 2 shows that the linewidth, and hence the signal stength of the $NH_3$ absorption, vary by only ±5% for the range of compositions typically encountered in flue gases from coal and oil fired furnaces, namely 10 to 15% $CO_2$, and 8 to 12% $H_2O$. FIG. 3 shows the dependence of the ammonia absorption coefficient at a nominal fixed flue gas composition (10% $H_2O$, 12% $CO_2$), for a temperature range of 0°–600° C. The data at 20° C. and over the range 260° C. to 300° C. were obtained by measuring the optical absorption of a known amount of ammonia in a flue gas mixture, using a tunable diode laser. By scaling populations and line widths to higher temperatures, absorption strengths to 600° C. are predicted as indicated. From FIG. 3 it is evident that in order to determine ammonia concentration to ±5% at 300° C. from absorption measurements, one must know the temperature of the flue gases to ±15° C.

FIG. 4 shows the difference in absorption coefficient of the flue gas—in the absence of $NH_3$—at two selected wavelengths, as a function of both temperature and composition. The absorption due to carbon dioxide at 260°–300° C. in a hot flue gas mixture was measured using a tunable diode laser. The data from 600°–900° K. are extrapolated from known room temperature data and the measured absorption values using known scaling laws. Since the presence of $NH_3$ is detected by a difference in absorption coefficient at these two wavelengths, the absorption difference due to the flue gas represents a zero level for the $NH_3$ measurement. As the composition and temperature of the flue gas changes, so does the zero level. Uncertainty in the zero level then limits the sensitivity of detection for $NH_3$. From FIG. 4 one calculates that at 900° K., a maximum expected variation from 10% to 15% in $CO_2$ concentration produces a corresponding uncertainty in $NH_3$ concentration of 3 parts per million. Thus the device of FIG. 1, which measures the temperature of the flue gas mixture but not its composition, can detect 5 parts per million of $NH_3$.

Flue gas temperature is readily monitored, whereas an in situ real time monitoring measurement of $H_2O$ and $CO_2$ concentrations in flue gas is a complex and costly procedure. The ability to forego the measurement of flue gas $CO_2$ and $H_2O$ composition and rely only on a measurement of the flue gas temperature in conjunction with the measurement of optical absorption makes this method practical for real-time (monitoring) applications.

What is claimed is:

1. A system for monitoring gaseous ammonia concentration in flue gases comprising:
   (a) a first laser means which emits radiation at about 927.30 cm$^{-1}$ which is selectively absorbed by ammonia but not spectrally selectively absorbed by any substance in said flue gases said flue gases including more than about 10% $CO_2$ and more than about 8% $H_2O$;
   (b) a second laser means which emits radiation which is not spectrally selectively absorbed by ammonia or by said flue gases;
   (c) means to measure the temperature of said flue gases;
   (d) means to modulate the output radiations of each of said first and second laser means;
   (e) means to measure each of the powers of the output radiations of said first and second laser means;
   (f) means to combine and direct a portion of each of said output radiations onto a common optical path through said flue gases;
   (g) means to measure the powers of each of said portion of said radiations after passing through said flue gases;
   (h) means to electronically measure the absorption of said radiations; and
   (i) means for computing the absolute concentration of said ammonia from said measurements of said absorption of said radiation and said measurements of said temperature.

2. The system of claim 1 wherein said laser means are $CO_2$ lasers.

3. The system of claim 1 wherein said second laser means emits radiation at 924.53 cm$^{-1}$.

* * * * *